(12) United States Patent
Ferraro et al.

(10) Patent No.: US 6,376,733 B1
(45) Date of Patent: *Apr. 23, 2002

(54) PROCESS FOR PRODUCTION OF PARAXYLENE

(75) Inventors: John Michael Ferraro; Robert Michael Osman; John Di-Yi Ou, all of Houston, TX (US); Graeme Ian Cox, Doncaster East (AU); James Richardson Lattner, Seabrook; Kenneth Ray Clem, Humble, both of TX (US)

(73) Assignee: ExxonMobil Chemical Patents Inc., Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/591,064

(22) Filed: Jan. 25, 1996

(51) Int. Cl.⁷ .............................. C07C 7/144; C07C 5/22
(52) U.S. Cl. ................. 585/805; 585/819; 585/477; 585/478; 585/481; 585/321
(58) Field of Search .................................. 585/805, 819, 585/477, 478, 481, 321; 502/4

(56) References Cited

U.S. PATENT DOCUMENTS

| | | | | |
|---|---|---|---|---|
| 3,504,048 A | | 3/1970 | Rosset ........................ | 260/674 |
| 3,548,017 A | * | 12/1970 | Hebert et al. ............... | 585/478 |
| 3,701,813 A | * | 10/1972 | Stenmark .................... | 585/315 |
| 4,101,595 A | * | 7/1978 | Chen et al. .................. | 585/321 |
| 4,101,597 A | * | 7/1978 | Breckenridge .............. | 585/321 |
| 5,019,263 A | * | 5/1991 | Haag et al. ............ | 210/500.25 |
| 5,069,794 A | * | 12/1991 | Haag et al. ................. | 210/650 |
| 5,100,596 A | * | 3/1992 | Haag et al. .................. | 264/42 |
| 5,110,478 A | * | 5/1992 | Haag et al. ................. | 210/650 |
| 5,474,681 A | * | 12/1995 | Fehlner et al. ......... | 210/500.25 |
| 5,618,435 A | * | 4/1997 | Fehlner et al. .............. | 210/651 |
| 5,716,527 A | * | 2/1998 | Deckman et al. ........... | 210/651 |

FOREIGN PATENT DOCUMENTS

| | | |
|---|---|---|
| WO | 8909642 | 10/1989 |
| WO | 94/25151 | 11/1994 |
| WO | 96/01686 | 1/1996 |

* cited by examiner

*Primary Examiner*—Walter D. Griffin

(57) ABSTRACT

This invention relates to a process and a chemical plant for the production primarily of paraxylene. In particular the process and chemical plant utilise zeolite membranes for enhanced paraxylene production.

21 Claims, 6 Drawing Sheets

PROCESS FOR PRODUCTION OF PARAXYLENE

BACKGROUND OF THE INVENTION

This invention relates to a process and a chemical plant for the production of paraxylene. In particular the process and chemical plant utilise zeolite membranes for enhanced paraxylene production.

In the petrochemical production chain one of the most important streams is the $C_6$ to $C_8$ aromatics stream which is a source of raw materials for high value downstream products. From this stream, benzene, toluene and the $C_8$ aromatics which are particularly valuable may be obtained. The $C_8$ aromatics are orthoxylene, metaxylene, paraxylene and ethylbenzene. Paraxylene is often the most desirable of the xylenes; however because the boiling points of ethylbenzene, ortho-, meta- and paraxylene (hereinafter collectively referred to as "$C_8$ aromatics") are close, they are difficult to separate by fractional distillation. As a consequence various alternative methods of separating paraxylene from $C_8$ aromatics have been developed. The most common of such methods are fractional crystallisation which utilises the difference in freezing points between ethylbenzene, ortho-, meta- and paraxylene, and selective adsorption which commonly utilises zeolite materials to selectively adsorb paraxylene from $C_8$ aromatics streams; the adsorbed paraxylene is recovered after desorbing from the zeolite. When either of these processes are used paraxylene can be recovered in high yields from the $C_8$ aromatics stream. The resulting filtrate from the crystallisation process or the raffinate from the adsorption process are depleted in paraxylene and contain relatively high proportions of ethylbenzene, ortho-, and metaxylene. These streams are typically subjected to further processing downstream of the crystallisation or adsorption process.

Typically one of the additional downstream processes is an isomerisation process which is used to increase the proportion of paraxylene in paraxylene depleted streams from such processes as fractional crystallisation or selective adsorption. The xylenes, which are predominantly ortho-and metaxylene, can be contacted with an isomerisation catalyst under appropriate temperature and pressure which results in the conversion of some of the ortho- and metaxylene to paraxylene. It is also usually necessary to convert some of the ethylbenzene to prevent it from building up to high concentrations. A catalyst can be selected to enable conversion of ethylbenzene to benzene, and/or to orthoxylene through a $C_8$ naphthene intermediate and/or to $C_{10}$ aromatics and benzene via transalkylation. It may be that the catalyst for conversion of ethylbenzene to orthoxylene is also a xylenes isomerisation catalyst in which case the orthoxylene from the ethylbenzene is converted to an equilibrium mixture of xylenes.

Prior art processes for making paraxylene have typically included combinations of isomerization with fractional crystallisation and/or adsorption separation. The problem with this combination is that despite improvements in catalyst performance the isomerisation technology is only able to produce equilibrium or near-equilibrium mixtures of xylenes and may also be relatively inefficient for the conversion of ethylbenzene to benzene or xylenes. The consequence of this is that big recycles of the xylenes stream back through these processes are needed to ensure the conversion of the $C_8$ aromatics stream to paraxylene is maximised with or without the additional recovery if desired of orthoxylene and/or metaxylene. There is a need therefore for improved processes and chemical plants for the production of paraxylene from $C_8$ aromatics streams, which in particular address the problems associated with large recycles and/or low ethylbenzene conversions.

Zeolite membranes have been described in the prior art, for example in U.S. Pat. No. 4,699,892, U.S. Pat. No. 5,100,596, EP 0481658, EP 0481659, EP 0481660, WO 92/13631, WO 93/00155, WO 94101209, and WO 94/25151. However the prior art does not describe how to use such membranes in actual $C_8$ aromatics processing in the petrochemical cycle nor does the prior art describe how to use such membranes in combination with existing processes to significantly enhance their paraxylene production capability

SUMMARY OF THE INVENTION

The present invention is therefore directed to a chemical plant and process which offers an improvement over the prior art for the production of paraxylene from $C_8$ aromatics streams. The present invention resides in the specific application of a zeolite membrane unit and process in a paraxylene or paraxylene with orthoxylene and/or metaxylene recovery process. This invention utilises zeolite membranes to continuously separate paraxylene and/or ethylbenzene from xylenes, or to isomerise ortho- and metaxylene to paraxylene and/or ethylbenzene to xylenes and simultaneously or subsequently separate paraxylene from the xylenes mixture. The use of a zeolite membrane unit and process in for example a process for paraxylene recovery provides for a significant improvement in paraxylene production when compared to conventional paraxylene recovery processes.

Accordingly the present invention provides a process for recovering paraxylene from a $C_8$ aromatics stream containing paraxylene and at least one other isomer of xylene, ethylbenzene, or mixtures thereof which process comprises:
(a) recovering by means of a paraxylene separation process in a paraxylene recovery unit a portion of said paraxylene from at least a portion of said $C_8$ aromatics stream to produce a first stream having a reduced paraxylene content and containing at least a portion of said other isomers of xylene, said ethylbenzene, or mixtures thereof;
(b) passing at least a portion of said first stream directly or indirectly to a zeolite membrane unit comprising a zeolite membrane and optionally isomerisation catalyst under isomerization conditions, such that the permeate withdrawn through the zeolite membrane and from the zeolite membrane unit is enriched in is paraxylene when compared to the feed to the zeolite membrane unit and
(c) feeding the permeate directly or indirectly back to the paraxylene separation process.

Preferably there is an additional step between (a) and (b) wherein at least a portion of said first stream is subjected to an isomerisation process in an isomerisation unit to produce an isomerate having an enriched paraxylene content compared to that of the first stream; and it is at least a portion of this isomerate stream which is passed to the zeolite membrane unit. Most preferably the permeate withdrawn from the zeolite membrane unit is enriched in paraxylene compared to the equilibrium concentration of paraxylene in a xylenes equilibrium mixture.

The present invention further provides for a paraxylene recovery plant comprising:
(a) paraxylene recovery unit, and
(b) a zeolite membrane unit comprising a zeolite membrane and optionally isomerisation catalyst.

Preferably the paraxylene recovery plant comprises an isomerisation unit in addition to the paraxylene recovery unit and zeolite membrane unit.

DETAILED DESCRIPTION OF THE INVENTION

The paraxylene recovery unit uses separation technology to produce a paraxylene enriched stream and a paraxylene depleted stream. Such separation technology includes for example the known processes of fractional crystallisation, or selective adsorption using for example molecular sieve absorbers. The paraxylene recovery unit may therefore be a fractional crystallisation unit which utilises the difference in freezing points between ethylbenzene, ortho-, meta- and paraxylene or it may be a selective adsorption unit which commonly utilises zeolite materials to selectively adsorb paraxylene from $C_8$ aromatics streams; the adsorbed paraxylene is recovered after desorbing from the zeolite. The paraxylene recovery unit may also be a combination of such separation units, or may incorporate other less commonly used techniques such as fractional distillation.

Fractional crystallisation units are well known in the art and are described for example in U.S. Pat. No. 4,120,911. Commercially available processes include the crystallisation Isofining process, direct contact $CO_2$ crystallisers, scraped drum crystallisers, and continuous countercurrent crystallisation processes. The crystalliser may operate for example in the manner described in Machell et. al. U.S. Pat, No. 3,662,013. Commercial fractional crystallisation processes typically recover about 60% to 68% of the paraxylene from the feed to the paraxylene recovery unit when this feed is an equilibrium or near equilibrium mixture of xylenes and ethylbenzene. The reason for this is that they are limited by the formation of a eutectic between paraxylene and metaxylene However the actual recovery depends on the composition of the feed with higher recoveries possible when the paraxylene content of the feed is higher than the xylenes equilibrium content.

Selective adsorption units are also well known in the art and are described for example in U.S. Pat. No. 3,706,812, U.S. Pat. No. 3,732,325, U.S. Pat. No. 4,886,929, and references cited therein, the disclosures of which are hereby incorporated by reference. Commercially available processes include UOP PAREX™, and IFP-Chevron ELUXYL™ processes. Commercial molecular sieve selective adsorption processes may recover higher levels of paraxylene than fractional crystallisation processes; typically they recover over 90% or more typically over 95% of the paraxylene from the feed to the paraxylene recovery unit.

The paraxylene recovery unit produces a paraxylene enriched stream that usually comprises over 99% and may even be as high as 99.9% paraxylene. The exact amount depends on the process used and the design and operating conditions of the specific plant. The balance in this stream being ethylbenzene, ortho-, and metaxylene, toluene, and $C_9$ aromatics, paraffin's, naphthenes and possibly small amounts of other materials. The paraxylene recovery also produces a paraxylene depleted stream containing the balance of ethylbenzene, ortho-, and metaxylene, toluene, $C_9$ aromatics, paraffins, etc. along with any paraxylene fed to the paraxylene recovery unit that is not removed in the paraxylene rich stream. It is this paraxylene depleted stream which is then fed to the isomerisation unit and/or zeolite membrane unit.

The $C_8$ aromatics stream which is used as the feed for the paraxylene separation unit may come from a variety of sources in the petrochemical plant. One possible source Is from naphtha reforming. Examples of such processes include Exxon POWERFORMING™, UOP Platforming™, IFP Aromizing™. Another possible source is pyrolysis gasoline from steam cracking processes although this is likely to be a minor source of such streams. A further possible source is the UOP Cyclar process for conversion of $C_3/C_4$ hydrocarbon streams to aromatics (see for example U.S. Pat. No. 5,258,563, the disclosure of which is hereby incorporated by reference). A further possible source is from toluene disproportionation and/or $C_9$ aromatics transalkylation. Examples of such processes include UOP TATORAY™, TORAY TAC9™, Mobil Selective Toluene Disproportionation™ (MSTDP), Mobil Toluene Disproportionation™ (MTDP), IFP Xylenes PLUS™ and FINA T2BX™. There are other possible sources of $C_8$ aromatics streams. The source of $C_8$ aromatics stream for the process of the present invention is not critical and may be a single stream or may be a combination of streams from any of the above processes.

The isomerisation unit may be any of the well known units in the art such as those described in U.S. Pat. No. 4,236,996, U.S. Pat. No. 4,163,028, U.S. Pat. No. 4,188,282, U.S. Pat. No. 4,224,141, U.S. Pat. No. 4,218,573, U.S. Pat. No. 4,236,996, U.S. Pat. No. 4,899,011, U.S. Pat. No. 3,856,872 and Re. 30,157, the disclosures of which are hereby incorporated by reference.

The isomerisation catalyst may be any of the well known catalysts for isomerisation units in the art. There are primarily two types of catalyst system which are used in isomerisation units. The choice of catalyst has an impact on the overall yield and structure of the aromatics complex and also on the plant design and economics. The first type of catalyst is designed to convert ethylbenzene to xylenes and to isomerise the paraxylene depleted feed stock to a near equilibrium xylene composition. This type of catalyst system is generally the choice for aromatics producers whose objective is to maximise para and ortho-xylene production from a fixed quantity of feed stock. A second catalyst system is also designed to isomerise the para xylene depleted feed stock; however rather than converting ethylbenzene to xylenes, this catalyst system dealkylates the ethylbenzene to produce benzene. This catalyst system is often employed when the benzene requirements are high relative to ortho and para xylene production or when feed stock availability is not a limiting factor.

Examples of processes and catalyst systems which include the capability of converting ethylbenzene to benzene are the Mobil MHTI (Mobil High Temperature Isomerisation) process and catalyst (see for example U.S. Pat. No. 3,856,871 and U.S. Pat. No. 4,638,105, the disclosures of which are hereby incorporated by reference), the Mobil MHAI (Mobil High Activity Isomerisation) process and catalyst, the AMOCO AMSAC process and catalyst and the UOP ISOMAR™ 1-100 process and catalyst.

Examples of processes and catalyst systems which include the capability of converting ethylbenzene to xylenes are the IFP/ENGELHARD Octafining and Octafining II processes and catalyst, and the UOP ISOMAR™ 1-9 process and catalyst. Other processes include catalysts capable of converting ethylbenzene to $C_{10}$ aromatics. Other processes do not include ethylbenzene conversion.

Isomerization units typically use a zeolite or mordenite type catalyst. Isomerization catalysts known to promote conversion of ortho and metaxylene to paraxylene include metal promoted molecular sieves such as for example Pt Promoted ZSM-5, Pt promoted Mordenite and metal promoted borosilicates etc. Commercial examples are Mobil MHAI and ISOMAR™ 1-9 catalyst.

The isomerization reactor is arranged and effective to isomerise ortho- and metaxylene to paraxylene at these conditions and also advantageously to convert ethylbenzene to benzene and/or xylenes. The term "arranged and effective" is used in this application to denote that conditions in a process unit are as described in this specification to include the temperatures, pressures, space velocities, reaction time, other reactants, and any other process conditions necessary to achieve the desired reaction, conversion or separation that is the normal function of that process unit.

Operating temperatures are typically in the range of 400 to 900° F. and pressures in the range of 25 to 500 PSIG The weight hourly space velocity (WHSV) based on hydrocarbon feed typically ranges from 0.5 to 20. Most isomerization catalyst systems require a source of hydrogen which can be introduced to the isomerization reactor to promote the isomerization reaction that converts ortho- and metaxylene to paraxylene, to assist in the conversion of ethylbenzene to benzene and or xylenes and assists also in the prevention of coking of the isomerisation catalyst.

In one aspect of the present invention the zeolite membrane unit is used to selectively separate paraxylene and/or ethylbenzene from a stream which comprises ethylbenzene and an equilibrium or near equilibrium mixture of xylenes. In this aspect the zeolite membrane unit may be located downstream of an isomerisation unit and does not have an isomerisation catalyst in combination with the membrane.

In a further aspect of the present invention, a zeolite membrane unit utilises an isomerisation catalyst in combination with the membrane to isomerise ortho- and metaxylene to paraxylene in co-operation with the selective separation function of the membrane and may also include the catalytic conversion of ethylbenzene to benzene or xylenes.

In this aspect of the present invention the zeolite membrane may itself be rendered catalytically active for the isomerisation reaction or an appropriate isomerisation catalyst may be located proximate to the membrane. By proximate to the membrane is meant that the catalyst is arranged and effective to isomerise the ortho- and/or metaxylene and/or ethylbenzene in the material in the zeolite membrane unit but upstream of the zeolite membrane to produce paraxylene. The exact amount of paraxylene which is required to be produced by the isomerisation process in the zeolite membrane unit depends in part on the properties of the zeolite membrane used. If the membrane for example has high flux and/or high selectivity for paraxylene then it may be possible or even desirable for the isomerisation reaction to produce and maintain paraxylene at a non equilibrium concentration compared to its concentration in an equilibrium xylene mixture whilst the membrane selectively removes paraxylene from the upstream material and into the permeate. However the isomerisation catalyst in the zeolite membrane unit should ideally be arranged and effective to produce and maintain paraxylene, upstream of the membrane and inside the zeolite membrane unit, at 50% or more, preferably 80% or more, and most preferably 90% or more of the paraxylene equilibrium concentration whilst the membrane selectively removes paraxylene from the upstream side of the membrane and into the permeate. Depending on membrane properties it may be desirable and preferable to maintain the paraxylene concentration at or near to equilibrium for xylenes isomerisation which the membrane selectively removes paraxylene from the retentate into the permeate. Thus the isomerisation catalyst causes the ortho-, and metaxylene to convert to paraxylene and the paraxylene selectively permeates through the zeolite membrane to be produced as a permeate stream. Ortho- and metaxylene less readily pass through the zeolite membrane and tend to stay on the upstream side in the retentate stream where they can be further isomerised. The permeate stream from xylenes isomerisation unit may be fractionated to remove materials boiling below and above the boiling point of xylenes e.g. benzene, toluene and C9+ aromatics and then transferred to the paraxylene recovery unit. If the zeolite membrane unit is particularly efficient at isomerisation -and separation there may theoretically be no retentate stream as there would be no paraxylene depleted stream to reject. In practice there will however likely be impurities and heavier aromatic compounds such as $C_9$ aromatics which remain in the retentate stream and must be purged from the zeolite membrane unit for further treatment. Thus in the zeolite membrane unit there is a dynamic and coupled process of isomerisation and separation of xylenes. If the catalytic function is also capable of converting ethylbenzene to benzene or xylenes then any ethylbenzene which enters into the retentate stream of the unit is also involved in this dynamic process with the resulting xylenes entering into the xylenes isomerisation reactions or the resulting benzene passing through the membrane into the permeate stream. In this aspect the zeolite membrane unit may be downstream of an isomerisation unit or may be used in place of an isomerisation unit.

In a further aspect the zeolite membrane is used to selectively separate ethylbenzene with a small amount of paraxylene from a paraxylene depleted feedstream as is typically found after a paraxylene separation process. In this aspect the zeolite membrane unit is located between the paraxylene separation unit and an ethylbenzene isomerisation unit. The feed to the isomerisation unit is enriched in ethylbenzene and improves the efficiency of the ethylbenzene isomerisation process in this unit. The output from this isomerisation unit is enriched in paraxylene and passes into a conventional paraxylene isomerisation unit along with the retentate from the zeolite membrane unit. In such a process the paraxylene isomerisation unit is required to convert lower levels of ethylbenzene and therefore may be operated at lower temperatures and may in fact be a liquid phase isomerisation unit which has no ethylbenzene conversion activity. The overall effect of this use of the zeolite membrane is to enhance the conversion of ethylbenzene to useful xylenes and to significantly reduce the xylene losses which usually occur due to the use of high temperature isomerisation units such as ISOMAR™ or MHTI™. A further modification of this aspect of the present invention is to include a catalytic function into the zeolite membrane unit. This catalytic function may be for ethylbenzene conversion and may be located within the membrane itself. This catalytic function may advantageously be located proximate to the membrane on the permeate side of the zeolite membrane. The function of this catalyst is to catalyse the conversion of ethylbenzene to xylenes. The effect of this is to deplete the concentration of ethylbenzene on the permeate side of the membrane and in doing so sets up a concentration gradient across the membrane which increases the quantity of ethylbenzene transferred from the retentate stream into the permeate stream. If the ethylbenzene conversion catalyst in the zeolite membrane unit is particularly efficient there may be no need for the ethylbenzene isomerisation unit which is located downstream of the zeolite membrane unit. In a further embodiment a second zeolite membrane unit for selective paraxylene separation or for selective paraxylene separation and isomerisation, may be located downstream of the paraxylene Isomerisation unit. The permeate stream from xylenes isomerisation unit or the second zeolite membrane unit if present may be fractionated to remove materials boiling below and above the boiling point of xylenes e.g.

benzene, toluene and C9+ aromatics and then transferred to the paraxylene recovery unit. Optionally, the retentate stream may be combined with the permeate stream and the combined streams fractionated and transferred to the paraxylene recovery unit for recovery of a paraxylene rich stream.

Examples of zeolite membranes which may be used in zeolite membrane units for the present invention are described in the following documents. U.S. Pat. No. 5,110,478, the disclosure of which is hereby incorporated by reference, describes the direct synthesis of zeolite membranes. The membranes produced in accordance with the teachings of U.S. Pat. No. 5,110,478 were discussed in "Synthesis and Characterisation of a Pure Zeolite Membrane," J. G. Tsikoyiannis and W. Haag, Zeolites (VOI. 12, p. 126., 1992) Such membranes are free standing and are not affixed or attached as layers to any supports. Zeolite membranes have also been grown on supports. See e.g. "High temperature stainless steel supported zeolite (MFI) membranes: Preparation, Module, Construction and Permeation Experiments," E. R. Geus, H. vanBekkum, J. A Moulyin, Microporous Materials, Vol. 1, p. 137, 1993; Netherlands Patent Application 91011048; European Patent Application 91309239.1 and U.S. Pat. No. 4,099,692, the disclosures of which are hereby incorporated by reference. Other literature describing supported inorganic crystalline molecular sieve layers includes U.S. Pat. No. 4,699,892; J. C. Jansen et al, Proceedings of 9th International Zeolite Conference 1992 (in which lateral and axial orientations of the crystals with respect to the support surface are described), J. Shi e al, Synthesis of Self-supporting Zeolite Films, 15th Annual Meeting of the British Zeolite Association, 1992, Poster Presentation (in which oriented Gmelinite crystal layers are described); and S. Feng et al, Nature, Apr. 28th 1994, p 834 (which discloses an oriented zeolite X analogue layer), the disclosures of which are hereby incorporated by reference.

Further examples of zeolite membranes which may be used in zeolite membrane units for the present invention are described in the following documents; International Application WO 94/25151, U.S. Ser. No. 267760 filed Jul. 8th 1994, PCT U.S. Pat. No. 95/08512, PCT U.S. Pat. No. 95/08514, PCT U.S. Pat. No. 95/08513, PCT EP96102704 and WO 94101209, the disclosures of which are hereby incorporated by reference. In our earlier International Application WO 94/25151 we have described a supported inorganic layer comprising optionally contiguous particles of a crystalline molecular sieve, the mean particle size being within the range of from 20 nm to 1 $\mu$m. The support is advantageously porous. When the pores of the support are covered to the extent that they are effectively closed, and the support is continuous, a molecular sieve membrane results; such membranes have the advantage that they may perform catalysis and separation simultaneously if desired. Preferred zeolite membranes are those which are prepared by the Inverted In-Situ-Crystallisation (I-ISC) process, or by using a GEL layer and a Low Alkaline synthesis solution using the Inverted In-Situ-Crystallisation process (GEL-LAI-ISC),or by using a Seeding Layer and a Low-Alkaline-synthesis solution using the Inverted In-Situ Crystallisation (S-LAI-ISC). These processes are described in U.S. Ser. No. 267760 filed Jul. 8th 1994, PCT U.S. Pat. No. 95/08512, PCT U.S. Pat. No. 95/08514, PCT U.S. Pat. No. 95/08513 and PCT EP95/02704. Zeolite compositions fabricated using the above described LAI-ISC, GEL-LAI-ISC, or S-LAI-ISC techniques can have dense zeolite layers in which the zeolite crystals are intergrown such that non-selective permeation pathways in these as-synthesised zeolite layers are virtually non-existent. The zeolite membranes described above may be incorporated into the zeolite membrane unit in the form of a module such as that described in WO 94/01209. It is envisaged that the zeolite membrane unit will contain at least one zeolite membrane which may or may not be catalytically active. If the membrane is not catalytically active for the desired process a suitable catalyst may be used in combination with the membrane. This catalyst may be located on the upstream side of the membrane or the downstream side of the membrane depending on the process and the nature and purpose of the catalyst. In one embodiment one or more membranes may be arranged with one or more catalysts to provide alternating membrane and catalyst regions in the zeolite membrane unit. In this arrangement the feedstream to the unit may for example pass through a membrane region with the retentate flowing to a catalyst containing region and then through a second membrane region to a second catalyst region. The exact number of membrane and catalyst regions will depend on the nature of the separations and catalyst processes desired. The separation and catalyst process may be substantially the same for each combination of catalyst and membrane or may be different.

It should be understood that two or more zeolite membrane units with or without isomerisation catalyst in close proximity to the zeolite membrane in each unit may be used in the processes of the present invention. Reference to zeolite membrane unit in this specification should also be taken to include embodiments where two or more zeolite membrane units may be used in sequence to each other with or without any further intervening processes or process units.

The zeolite membrane unit may be installed downstream of an existing xylenes isomerization reactor or installed as a replacement of an isomerization reactor in an existing paraxylene recovery process. The zeolite membrane unit may be added to an existing process solely for separation of paraxylene from xylenes, or for both isomerization and separation. The most preferred option is to have the zeolite membrane unit downstream of a xylenes isomerisation unit and for the zeolite membrane unit to comprise a zeolite membrane and an isomerisation catalyst so that it performs both isomerisation of xylenes, and selective separation of paraxylene; optionally it also catalyses conversion of ethylbenzene to xylenes or benzene. If the zeolite membrane unit catalyses conversion of ethylbenzene to xylenes or benzene then this may allow less conversion of ethylbenzene in the conventional isomerisation unit with less xylene losses due to the lower operating temperature which would be required in the conventional isomerisation unit.

It is preferred that the zeolite membrane unit is incorporated into a conventional xylene recovery loop such as that shown in FIG. 1 and discussed below. The xylene recovery process is referred to as a "loop" because xylenes not converted to paraxylene are recycled to the isomerization unit that is usually a part of the xylene recovery loop again and again until the xylenes are converted to paraxylene and removed from the loop via the paraxylene separation unit. In such a loop orthoxylene may also be a product which is removed from the loop in the xylene splitter if desired. Orthoxylene can sometimes be generated by the isomerisation unit if the feed to that unit has a less than equilibrium orthoxylene concentration.

As indicated above the fresh feed for the xylene recovery loop may come from a variety of sources in the petrochemical cycle. Fresh feed from, for example, a reformer, which is introduced to the xylene recovery loop is usually fractionated before introduction to the paraxylene separation unit to remove materials boiling below the boiling point of xylenes, and may optionally also be fractionated to remove at least part of the material boiling above the boiling point of xylenes. If lower boiling materials are not removed from the fresh feed, it is introduced to a detoluenizer tower ("DETOL") which removes toluene and lighter materials by distillation. The feed is then introduced to either a xylene rerun tower or splitter. A xylene rerun tower removes $C_{9+}$ aromatics from the feed. A xylene splitter tower in addition removes at least part of the orthoxylene for subsequent recovery as orthoxylene product in an orthoxylene rerun tower. The fresh feed in a xylenes loop is combined with a recycle stream which comes from the xylene isomerisation unit or in the present invention from the zeolite membrane unit. The overhead stream from the xylene rerun tower or splitter is typically a mixture of compounds which includes 0 to 10 wt % non aromatics, 0 to 5 wt % toluene, 5 to 20 wt % ethylbenzene, 0 to 10 wt % $C_8$ naphthenes, and 70 to 95 wt % xylenes. The exact composition will depend on the fresh feed and the nature of the catalysts used in the isomerisation unit and in the zeolite membrane unit. It should be appreciated that the fresh feed to the xylenes recovery loop could be a combination of two or more feeds such as those discussed above. Thus it could be a combination of a feed from a naphtha reformer with that from a TATORAY™ or MSTDP™ unit.

It should be understood that in the present description when reference is made to a feed to, or material upstream of the membrane, in a zeolite membrane unit being at equilibrium in xylenes this means that it can be a mixture of xylenes which are at the typical respective concentrations for an equilibrium mixture of xylenes as known in the art. In the same context by near equilibrium is meant a composition comprising xylenes in which one or more of the xylenes present are at their none equilibrium concentration with respect to the other xylenes present and includes mixtures where one or more of the xylene isomers are present at a concentration which is greater than their equilibrium concentration. Ideally in such mixtures the paraxylene should be present at 50% or more, preferably 80% or more and most preferably at 90% or more of the paraxylene equilibrium concentration.

Other objects and features of the invention are described in the following detailed description wherein reference is made to the accompanying figures.

BRIEF DESCRIPTION OF THE DRAWINGS

In FIG. 1 fresh feed containing xylenes is introduced to a xylene splitter 2 through fresh feed line 1. A bottom stream 3 is withdrawn from the xylene splitter 2 containing materials having boiling points above xylenes and possibly containing orthoxylene. An overhead stream 4 is withdrawn from the xylene splitter containing xylenes and ethylbenzene. The overhead stream 4 is fed to paraxylene recovery unit 5. Xylenes are separated in paraxylene recovery unit 5 to yield a paraxylene rich stream 6 and a paraxylene poor stream 7. The paraxylene recovery unit normally uses fractional crystallisation and/or molecular sieve separation to separate paraxylene from other stream 4 components. The paraxylene poor stream 7 is then introduced to an isomerization (ISOM) unit 8 which contains an isomerization catalyst arranged and effective to promote isomerization of ortho and metaxylene to paraxylene and the conversion of ethylbenzenes to benzene and/or xylenes or other compounds. The isomerate 9 from the isomerisation unit 8 is then introduced to stabiliser 10. Stabiliser 10 separates five carbon and lighter compounds from stream 9 through differences in boiling points. Five carbon and lighter compounds are withdrawn from stabiliser 10 through line 11 and six carbon and heavier compounds are withdrawn from stabiliser 10 through line 12. The stream in line 12 is introduced to a DETOL unit 13 to remove toluene and lighter compounds through line 14. Xylenes and heavier materials are withdrawn from DETOL unit 13 through line 15 and introduced to xylene splitter 2. Normally fresh feed 2 and the xylenes withdrawn from the DETOL 13 through line 15 are passed through clay treaters which in order to simplify the figures are not shown in FIGS. 1 to 6. As an alternative to the splitter 2 described in FIG. 1 a rerun tower may be used. It is to be understood that when reference is made to a splitter. In this specification that this reference also encompasses the use of a rerun tower in place of the splitter. For the purposes of this application the description "splitter" shall be used when substantial orthoxylene is removed in the bottoms and "rerun" shall be used when it is not.

There are a number of disadvantages associated with this conventional process arrangement for paraxylene recovery. The first is that this combination of process steps requires a significant recycle through the loop in order to remove the maximum possible amounts of paraxylene. This Is primarily due to the fact that the isomerisation unit and processes are only able to produce equilibrium or near equilibrium mixture of xylenes for the recycle in the isomerate. A typical concentration of paraxylene in the isomerate from such a unit is 22 wt %. Another problem is that in most isomerisation processes there are xylenes losses of up to 4% or higher. Thus with repeated recycles this loss of xylenes to undesirable products may be significant.

Figure 2:
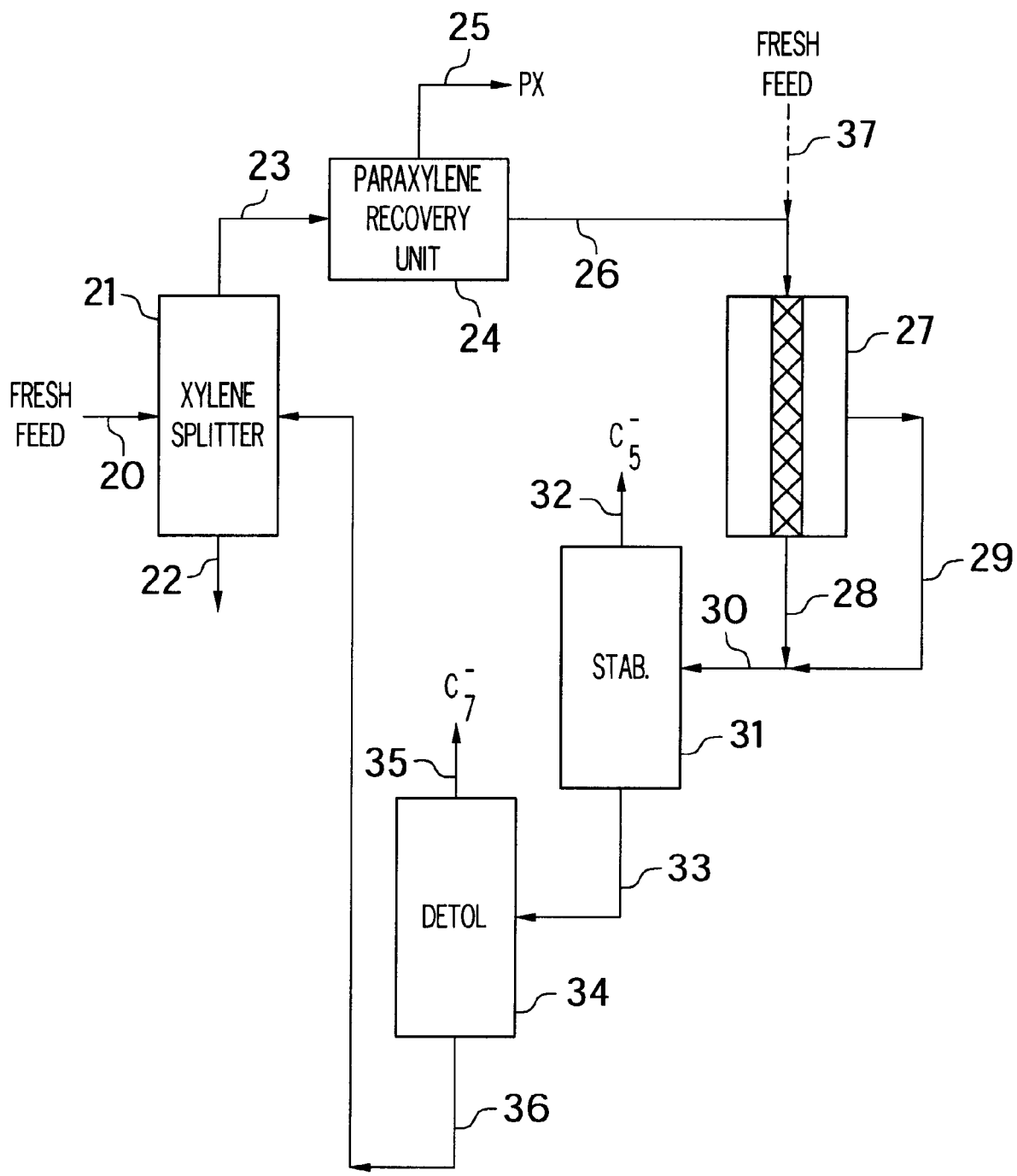
FIG. 2 shows a xylene purification loop utilising a zeolite membrane unit.

FIG. 2 shows a xylene purification loop according to the present invention. Fresh feed containing xylenes is introduced to a xylene splitter 21 through fresh feed line 20. A bottom stream 22 is withdrawn from xylene splitter 21 containing materials having boiling points above xylenes and possibly containing orthoxylene. An overhead stream 23 is withdrawn from the xylene splitter containing xylenes and ethylbenzene. The overhead stream 23 is fed to paraxylene recovery unit 24. Xylenes are separated in paraxylene recovery unit 24 to yield a paraxylene rich stream 25 and a paraxylene poor stream 26. The paraxylene recovery unit normally uses fractional crystallisation and/or molecular sieve separation to separate paraxylene from other stream 23 components. The paraxylene poor stream 26 is then introduced to zeolite membrane unit 27. Zeolite membrane unit 27 includes catalyst arranged and effective to promote isomerization of ortho- and metaxylene to paraxylene and the conversion of ethylbenzenes to benzene and/or xylenes or other compounds. The zeolite membrane also selectively permits permeation of paraxylene through the membrane relative to ortho- and metaxylene. A stream enriched in paraxylene is withdrawn from zeolite membrane unit 27 as permeate stream 28. The remaining material In retentate stream 29 should ideally be at equilibrium or near equilibrium in xylenes. The permeate stream 28 and retentate stream 29 may be treated separately (not shown in FIG. 2) or combined to form combined feed 30 and introduced to stabiliser 31. Stabiliser 31 separates five carbon and lighter compounds from stream 30 through differences in boiling points. Five carbon and lighter compounds are withdrawn from stabiliser 31 through line 32 and six carbon and heavier compounds are withdrawn from stabiliser 31 through line 33. The stream in line 33 is introduced to a DETOL unit 34 to remove toluene and lighter compounds through line 35. Xylenes and heavier materials are withdrawn from DETOL unit 34 through line 36 and introduced to xylene splitter 21. In addition it is also possible to introduce all or some of the fresh feed directly into the zeolite membrane unit 27 as indicated at line 37. This would have the advantage of further increasing the concentration of paraxylene in the paraxylene recovery unit feed, because a higher proportion of that feed would be derived from the zeolite membrane unit product rather than from the fresh feed having only an equilibrium or near equilibrium paraxylene concentration. However this approach requires a larger zeolite membrane unit, and may require a larger retentate stream to purge heavy aromatics brought in with the fresh feed, so there is an economic optimum for each application regarding how much, if any of the fresh feed to route directly to the zeolite membrane unit. For example in a retrofit situation where the paraxylene recovery unit capacity is limiting the plant production rate, it would likely be advantageous to route at least a portion of fresh feed to the zeolite membrane unit.

Figure 1:
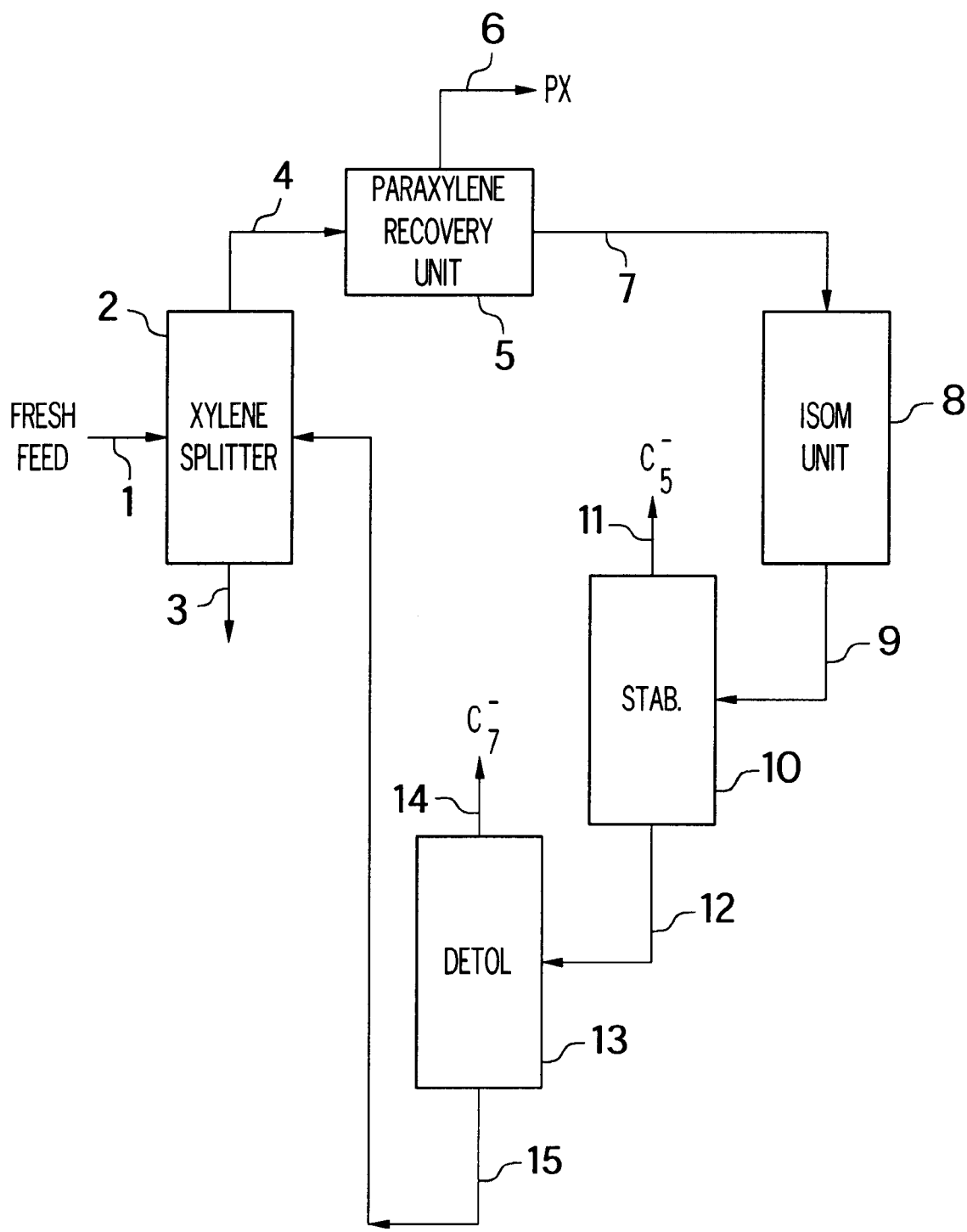
FIG. 1 shows conventional xylenes loop comprising a paraxylene separation unit and an isomerisation unit.

This embodiment of the present invention has a significant advantage over the conventional process as described in FIG. 1. The zeolite membrane unit produces a permeate with a greater than equilibrium amount of paraxylene and a retentate which has an equilibrium or near equilibrium concentration. The combined products will have a higher paraxylene content than is possible with the conventional isomerisation unit, which is limited by equilibrium. When those streams are recycled to the paraxylene recovery unit via the xylene splitter the paraxylene concentration is increased there, increasing per pass paraxylene recovery and reducing recycle which is a problem with conventional processes. In this embodiment the zeolite membrane unit is required to relatively efficiently isomerise xylenes and convert ethylbenzene and requires a zeolite membrane which has selectivity for paraxylene and exhibits acceptable flux through the membrane. Such membranes may be prepared using the LAI-ISC, S-IAI-ISC and GEL-LAI-ISC methods described above.

Figure 3:
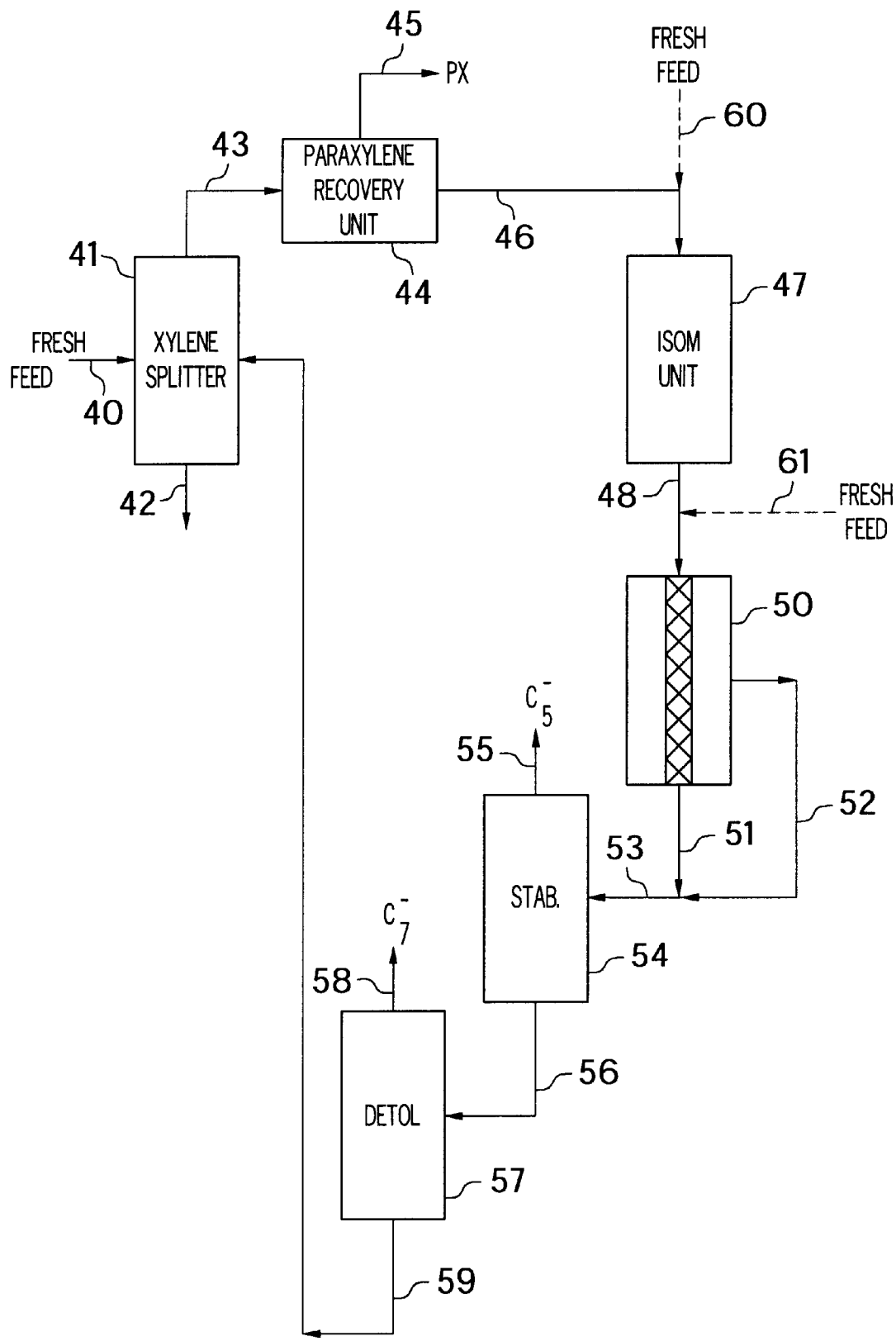
FIG. 3 is a xylene purification loop utilising a zeolite membrane unit downstream of an isomerization unit.

The particularly preferred embodiment of the invention is shown in FIG. 3. Fresh feed containing xylenes is introduced to xylene splitter through fresh feed line 40. A bottom stream containing 9 carbon and heavier compounds and possibly containing orthoxylene is withdrawn from xylene splitter through line 42. An overhead stream containing xylenes and ethylbenzene is withdrawn from xylene splitter 41 through line 43 and introduced to paraxylene recovery unit 44. Paraxylene is recovered in a paraxylene rich stream 45 while ortho- and metaxylene are recovered in paraxylene poor stream 46. The paraxylene poor stream 46 is introduced to an isomerization unit 47 which contains an isomerization catalyst arranged and effective to promote isomerization of ortho and metaxylene to paraxylene and the conversion of ethylbenzenes to benzene and/or xylenes or other compounds. Isomerised product is withdrawn through line 48 and introduced to zeolite membrane unit 49 containing zeolite membrane, catalyst that both isomerises ortho- and metaxylene to paraxylene and in which unit there is selective permeation of paraxylene through the zeolite membrane relative to ortho- and metaxylene. It should be noted that in this embodiment the catalyst may be incorporated into the membrane or the membrane itself may be catalytically active or rendered catalytically active or preferably it may be located on the upstream or inlet side of the membrane but in close proximity to the membrane. A stream enriched in paraxylene is withdrawn from zeolite membrane unit 50 through permeate stream 51. The remaining material leaves in retentate stream 52. Permeate stream 51 and retentate stream 52 may be treated differently (not shown in FIG. 3) or they may be combined in line 53 and introduced to stabiliser 54. Stabiliser 54 separates five carbon and lighter compounds from stream 53 through differences in boiling points. Five carbon and lighter compounds are withdrawn from stabiliser 54 through line 55 and six carbon and heavier compounds are withdrawn from stabiliser 54 through line 56. The stream in line 56 is introduced to a DETOL unit 57 to remove toluene and lighter compounds through line 58. Xylenes and heavier materials are withdrawn from DETOL unit 57 through line 59 and introduced to xylene splitter 41. In addition it is also possible for some or all of the fresh feed to be introduced to the isomerisation unit 47 or to the zeolite membrane unit 50 or to both as indicated at lines 60 and/or 61. The reason for using such a split feed has already been discussed above In relation to FIG. 2. Diverting fresh feed to either the isomerisation unit via line 60 or the zeolite membrane unit via line 61 would have similar benefits In terms of reduced xylene loop recycle. Using line 61 reduces flow through the isomerisation unit versus that required if line 60 is used. However it may still be advantageous to utilise line 60, since then it would combine with the feed in line 46 and could use the same pumps and/or reactor preheating equipment. This may be particularly advantageous if the zeolite membrane unit and the Isomerisation unit operate under similar conditions where isomerisation unit effluent flows directly to the zeolite membrane unit without the need for heating, cooling and/or pressure change. In that situation, stream 53 would typically be cooled by transferring its heat to the isomerisation unit feed to provide at least part of the reactor preheat. Such feed/effluent heat exchange systems usually work at their most efficient when feed and effluent flow rates are approximately the same. The optimum distribution of fresh feed amongst lines 40, 60 and 61 will vary depending on plant constraints and economic factors, and should be determined for each individual application. Conventional processes without zeolite membrane units have less flexibility in the routing of the fresh feed into the xylenes loop.

This particularly preferred embodiment not only has significant advantages over the prior art process of FIG. 1 but also has some significant advantages over that of FIG. 2. The combination of the isomerisation unit and the zeolite membrane unit downstream of the isomerisation unit enables the beneficial attributes of both units to be combined for maximum paraxylene production. The embodiment in FIG. 2 requires a particularly efficient zeolite membrane unit, as the feed to this unit which is derived from the paraxylene recovery unit is significantly depleted in paraxylene. The paraxylene content may be as low as 1% or less with the balance being mainly ortho- and metaxylene, ethylbenzene and minor amounts of other materials. This means that the zeolite membrane unit must be able to quickly isomerise this feed to produce the required amount of paraxylene on the upstream side of the membrane which exact concentration of paraxylene depends on the membrane properties and in some case will need to be an equilibrium or near equilibrium mixture of xylenes to achieve maximum efficiency in the process. Furthermore the zeolite membrane unit must also efficiently convert ethylbenzene or this will build up in the xylenes loop. The use of an isomerisation unit in combination with the zeolite membrane unit in FIG. 3 overcomes these deficiencies with the embodiment of FIG. 2. Firstly the isomerate from the isomerisation unit is already enriched In paraxylene and is typically at equilibrium or near equilibrium with respect to xylenes. This means that the zeolite membrane unit only has to maintain the Isomerate in or near this state to enable the membrane to work efficiently. Secondly because the isomerisation unit has the capability of ethylbenzene conversion, the ability of the zeolite membrane unit to destroy ethylbenzene, although desirable is not critical. Typically promoting xylenes equilibrium is easier than destroying ethylbenzene. The negative aspect of xylene losses which normally occur in the isomerisation unit is offset by the greatly reduced recycle needed when using the zeolite membrane unit in this embodiment. Also if the zeolite membrane unit does have at least some ethylbenzene conversion capability the Isomerisation unit does not have to do as much of this conversion. This would allow for the isomerisation unit to be operated under milder conditions and therefore result in less xylenes loss in the isomerisation unit. Also because there Is no need to for the feed to the zeolite membrane unit to be brought to equilibrium in this unit, as is required with some membranes when used in FIG. 2 embodiment, it may need significantly less catalyst and be significantly smaller in size compared to the zeolite membrane unit which is required for FIG. 2. In the particularly preferred embodiment of FIG. 3 when a membrane of selectivity of 5 for paraxylene/(ortho- and metaxylene) and a flux of greater than 10 $Kg/m^2/day$ is used the predicted level of paraxylene in the feed leaving the zeolite membrane unit compared to the isomerate leaving the isomerisation unit is 55 wt % compared to 22 wt % (the equilibrium concentration if about 10 wt % nonxylenes are present). This provides for an overall increase in paraxylene production in the cycle of 50% or more. Suitable membranes for use in a zeolite membrane unit to provide such improved performance are described for example in U.S. Ser. No. 267760 filed Jul. 8th 1994, PCT U.S. Pat. No. 95/08512, PCT U.S. Pat. No. 95/08514, PCT U.S. Pat. No. 95/08513 and PCT EP95/02704.

Figure 4:
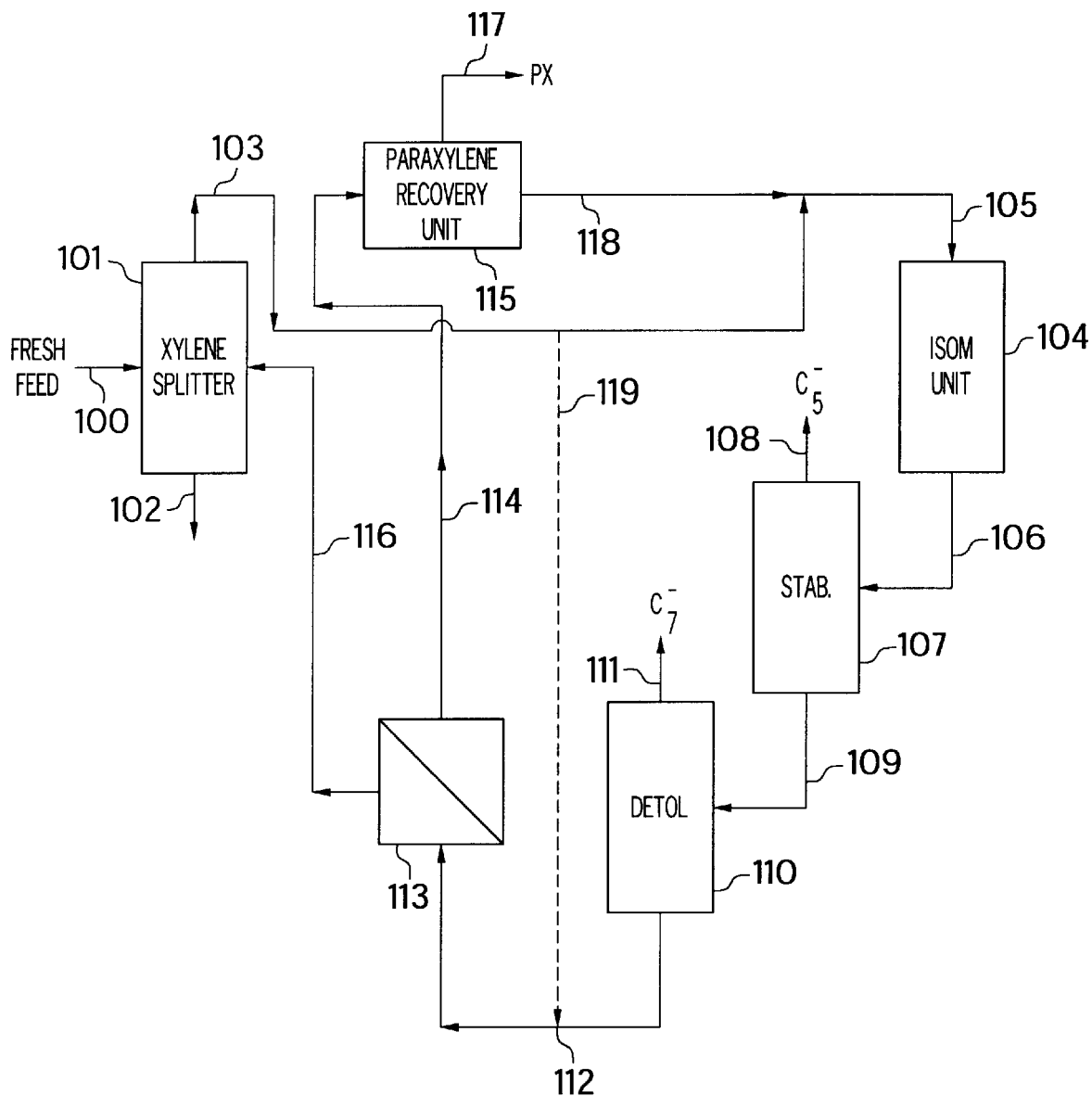
FIG. 4 shows a xylene purification loop utilising an isomerization unit upstream of a zeolite membrane unit without isomerisation catalyst and used for separating a paraxylene enriched stream that is transferred to a paraxylene recovery unit.

FIG. 4 shows an embodiment of the invention using a zeolite membrane to separate paraxylene from a xylene stream. Fresh feed containing xylenes is introduced to xylene splitter 101 through fresh feed line 100. Compounds boiling above xylenes and possibly including orthoxylene are withdrawn through bottom stream 102 and xylene and lighter boiling compounds are withdrawn as overhead stream 103. Overhead stream 103 is Introduced to isomerization unit 104 through intermediate line 105. The isomerization unit 104 converts ortho- and metaxylene to paraxylene and promotes the conversion of ethylbenzenes to benzene and/or xylenes or other compounds. Unconverted ortho- and metaxylene along with paraxylene are withdrawn from isomerization unit 104 through line 106 and introduced to stabiliser 107. 5 carbon and lighter boiling compounds are withdrawn from stabiliser 107 through line 108 with the balance of material withdrawn through line 109 and introduced to DETOL unit 110. Toluene and lighter boiling compounds are withdrawn from DETOL unit 110 through line 111 and xylenes are withdrawn through line 112 and introduced to zeolite membrane unit 113. Zeolite membrane unit 113 comprises a zeolite membrane that is arranged and effective to permit selective permeation of paraxylene relative to ortho- and metaxylene Most paraxylene is withdrawn through permeate stream 114 and Introduced to paraxylene recovery unit 115. Most ortho- and metaxylene are withdrawn from zeolite membrane unit 113 through retentate stream 116 and introduced to xylene splitter 101. The paraxylene recovery unit 115 separates paraxylene from ortho- metaxylene. Paraxylene is withdrawn through paraxylene rich stream 117 and the balance of ortho- and metaxylene are withdrawn through paraxylene poor stream 118. Paraxylene poor stream 118 is introduced to isomerization reactor 104 through line 105. Alternatively all or part of overhead stream 103 may be directed to the zeolite membrane unit 113 via line 119 and 112. The optimal routing of stream 103 depends on an economic balance amongst several parameters, namely isomerisation unit, per pass xylenes losses and ethylbenzene conversion and the zeolite membrane unit's relative selectivity between paraxylene and ethylbenzene. Routing steam 103 to zeolite membrane unit 113 has the advantage of avoiding whatever xylenes losses it would have incurred if it had been passed through the isomerisation unit 104. However there is a potential risk in this instance that ethylbenzene will build up in the xylenes loop. For example if zeolite membrane unit 113 ensured that all the ethylbenzene was retained in the retentate 116 the ethylbenzene would be retained in the xylenes loop without removal or destruction and would build up indefinitely as additional ethylbenzene is brought into the loop in the fresh feed. However if the selectivity of the zeolite membrane in the unit was such that a substantial portion of the ethylbenzene permeated through the membrane and into stream 114 then that portion of the ethylbenzene would pass to the isomerisation unit 104 via lines 115, 118 and 105, where some of it would be converted thus limiting its build up in the xylenes loop. There is also the possibility of an intermediate case where a portion of the stream 103 passes to the zeolite membrane unit and the remainder flows to the isomerisation unit. In this case the flow to the isomerisation unit acts as a purge to prevent the build up of ethylbenzene to unacceptable levels if the amount permeating through the membrane in the membrane unit is insufficient. the optimal balance should be determined for each specific application and will depend on the membrane properties and the properties of the xylenes isomerisation catalyst amongst others.

Figure 5:
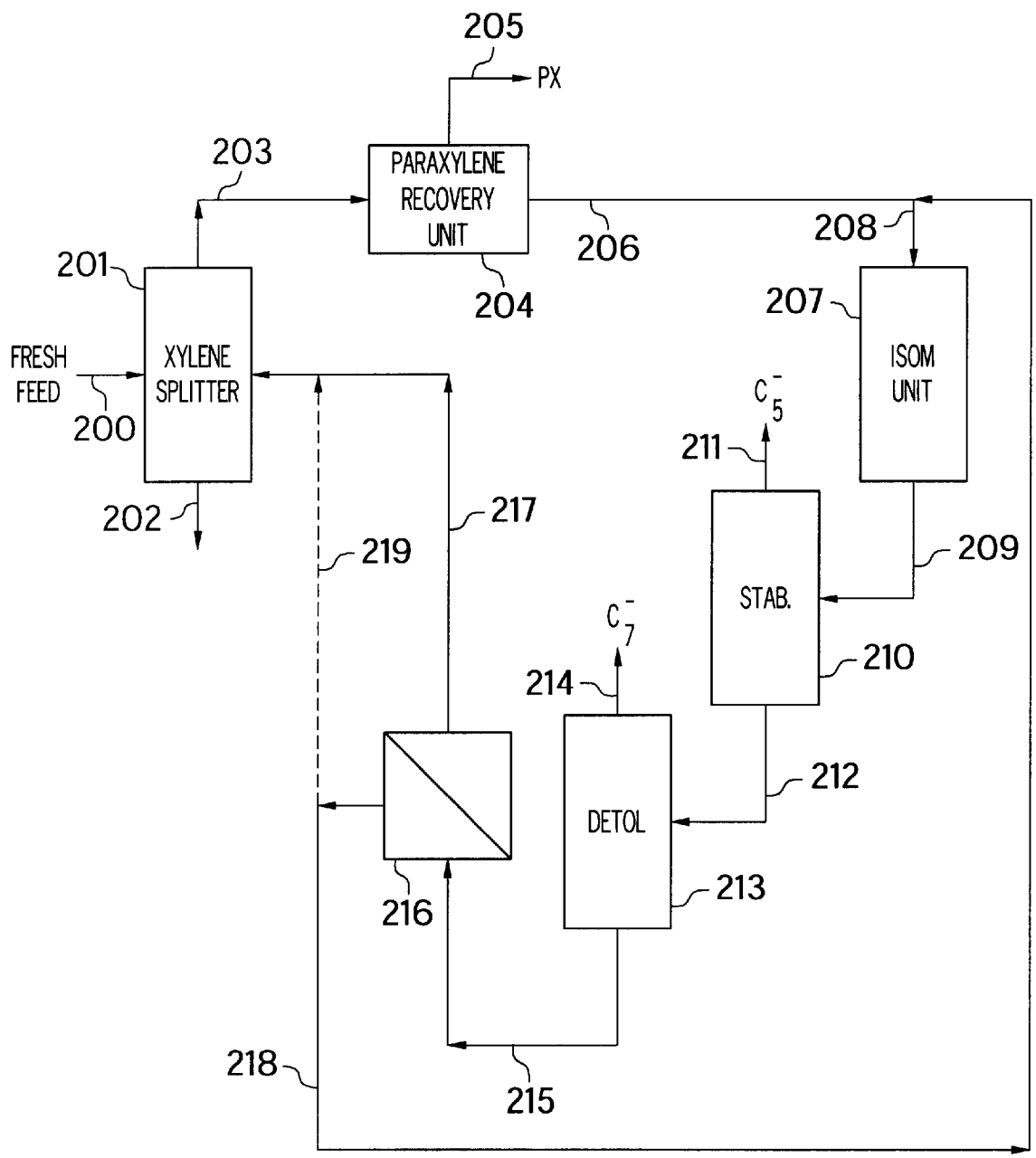
FIG. 5 shows a xylene purification loop having an isomerization unit upstream from a zeolite membrane unit without isomerisation catalyst and used for separating a paraxylene enriched stream that is then transferred to a xylene splitter.

Another embodiment of the invention is shown in FIG. 5 wherein xylenes are introduced to xylene splitter 201 through fresh feed line 200. Compounds boiling above the boiling point of xylenes and possibly some of the orthoxylene are withdrawn from xylene splitter 201 through bottoms line 202, xylenes and ethylbenzene are withdrawn through overhead stream 203 and introduced to paraxylene recovery unit 204 Paraxylene is withdrawn through paraxylene rich stream 205 and ortho- and metaxylene are withdrawn through paraxylene poor stream 206. Paraxylene poor stream 206 is introduced to an isomerization unit 207 through line 208. Isomerization unit 207 isomerises ortho- and metaxylene to paraxylene and promotes the conversion of ethylbenzene to benzene and/or xylenes or other compounds. The isomerate is withdrawn through line 209. The isomerate mixture which contains a near equilibrium mixture of ortho-, meta- and paraxylene is introduced to stabiliser 210 through line 209. 5 carbon and lighter compounds are withdrawn through line 211 and heavier boiling compounds are withdrawn through line 212 and introduced to DETOL unit 213. Toluene and lighter boiling compounds are withdrawn through line 214, xylenes and heavier materials are withdrawn from the DETOL unit 213 through line 215. Xylenes and heavier materials in line 215 are introduced to zeolite membrane unit 216 which comprises a zeolite membrane arranged and effective to permit selective permeation of paraxylene there through. Most paraxylene is withdrawn through line 217 and introduced to xylene splitter 201. Ortho- and metaxylene are withdrawn as retentate stream 218 and reintroduced to isomerization unit 207 through line 208. However it will likely be necessary to purge a portion of this stream to xylene splitter 201 via line 219 to avoid an excessive build up of C9+ aromatics as they will tend to stay in the retentate and not be removed in the stabiliser or DETOL units.

Figure 6:
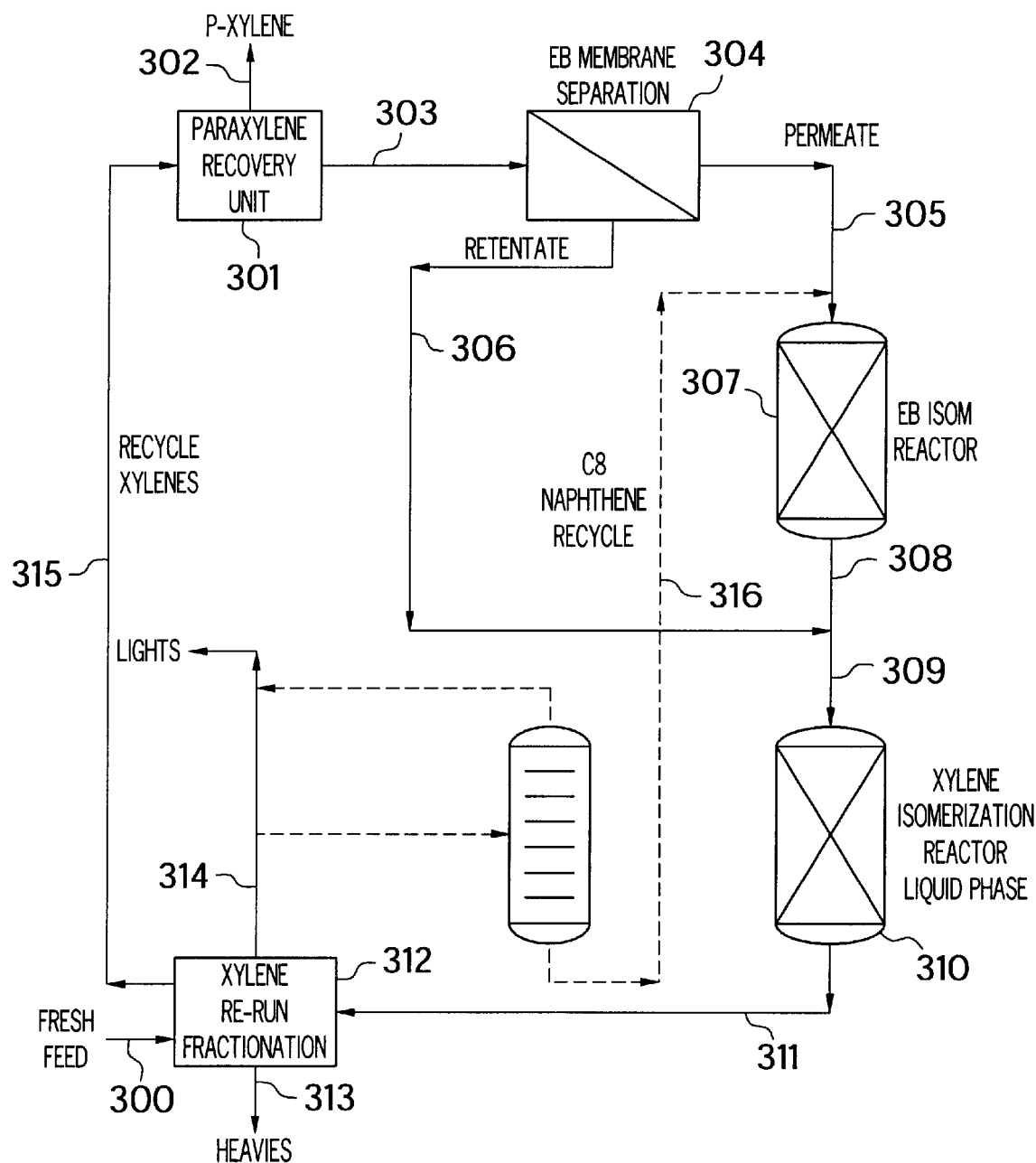
FIG. 6 shows a xylene purification loop which utilises an ethylbenzene membrane separation unit upstream of an ethylbenzene isomerisation unit which is upstream of an xylene isomerisation unit.

A further embodiment of the invention is shown in FIG. 6. In this embodiment the zeolite membrane unit has as its primary function the separation of ethylbenzene from a paraxylene depleted stream so that this may be passed into an ethylbenzene isomerisation unit. Thus a feed comprising xylenes and ethylbenzene 300 is passed to a xylene re-run fractionation sequence 312 and into a paraxylene recovery unit 301 via line 315. Paraxylene is withdrawn through paraxylene rich stream 302 and ortho- and metaxylene and ethylbenzene are withdrawn through paraxylene poor stream 303. Paraxylene poor stream 303 is introduced to a zeolite membrane unit 304 comprising a zeolite membrane which permits selective permeation of ethylbenzene and possibly paraxylene through the zeolite membrane relative to ortho- and metaxylene. Most of the ethylbenzene and possibly most of the paraxylene is withdrawn from the zeolite membrane unit 304 through permeate stream 305 and most of the ortho- and metaxylene are withdrawn through retentate stream 306. Permeate stream 305 passes into an ethylbenzene isomerisation unit 307. Ethylbenzene isomerization unit 307 isomerises ethylbenzene to xylenes The ethylbenzene isomerate is withdrawn through line 308. The retentate 306 and ethylbenzene isomerate 308 are combined to provide a unified feed 309 to the isomerisation unit 310 which may be a liquid phase xylenes isomerisation unit operating at 200° C. The xylenes isomerate passes from the isomerisation unit 310 through line 311 to a xylene re-run fractionation sequence 312 which produces a heavy stream 313, a lights stream 314 and a xylenes recycle 315. The lights stream may be further treated to a fractionation process to produce a $C_8$ naphthene recycle 316 to the ethylbenzene isomerisation unit 307 (shown as dotted lines in the figure). A possible addition to the process described in FIG. 6 is the inclusion of a zeolite membrane unit after the isomerisation unit 310 but before the xylene re-run fractionation sequence 312. This additional zeolite membrane unit would further enrich the stream 311 in paraxylene.

In this embodiment for a given membrane the predicted recovery of ethylbenzene on the permeate side of the membrane is 44 wt % compared to a normal ethylbenzene concentration of 6 to 7 wt %. The ethylbenzene conversion across the ethylbenzene isomerisation unit is 85% which compares favourably with a conventional process where the per pass conversion is 42%. Because a much smaller portion of the xylene loop is subjected to the severe conditions of the ethylbenzene isomerisation unit there are lower overall xylene losses. Also because the xylenes isomerisation unit conditions are less severe than in a combined ethylbenzene/xylenes isomerisation unit the losses of xylenes in this unit are significantly lower; 1% compared to 3 to 4%. This results in an overall yield for paraxylene for this embodiment of 94.5% compared to 84.5% for the conventional xylene loop without zeolite membrane unit. An additional advantage of this embodiment is that the amount of hydrogen circulation is dramatically reduced as the ethylbenzene conversion is in a separate reactor and hydrogen is not required for the xylenes isomerisation unit. This may result in a significant savings on the cost of operating a paraxylene recovery process according to this embodiment compared to the conventional xylenes loop.

What is claimed is:

1. A process for recovering paraxylene from a $C_8$ aromatics stream containing paraxylene and at least one other isomer of xylene, ethylbenzene, or mixtures thereof which process comprises:

(a) recovering by means of a paraxylene separation process in a paraxylene recovery unit a portion of said paraxylene from at least a portion of said $C_8$ aromatics stream to produce a first stream having a reduced paraxylene content and containing a portion of said other isomers of xylene, said ethylbenzene, or mixtures thereof;

(b) passing at least a portion of said first stream to an isomerization unit to produce an isomerate having an enriched paraxylene content compared to that of said first stream;

(c) passing at least a portion of said isomerate directly or indirectly to a membrane unit comprising a molecular sieve membrane and optionally isomerization catalyst under isomerization conditions, such that the permeate withdrawn through the molecular sieve membrane and from the molecular sieve membrane unit is enriched in paraxylene when compared to the feed to the membrane unit; and (d) feeding the permeate directly or indirectly back to the paraxylene separation process.

2. A process as claimed in claim 1 wherein the permeate withdrawn from the molecular sieve membrane unit is enriched in paraxylene compared to the equilibrium concentration of paraxylene in a xylenes equilibrium mixture.

3. A process as claimed in claim 1 wherein the paraxylene recovery unit comprises a fractional crystallisation unit.

4. A process as claimed in claim 1 wherein the paraxylene recovery unit comprises an adsorption separation unit.

5. A process as claimed in claim 1 wherein the paraxylene recovery unit comprises an adsorption separation unit in combination with a fractional crystallisation unit.

6. A process as claimed in claim 1 wherein the molecular sieve membrane unit isomerises metaxylene and orthoxylene to paraxylene.

7. A process as claimed in claim 1 wherein the molecular sieve membrane unit converts ethylbenzene to benzene and/or xylenes and/or $C_{10}$ aromatics.

8. A process as claimed in claim 1 wherein the molecular sieve membrane unit comprises a zeolite membrane which is active as an isomerization catalyst.

9. A process as claimed in claim 1 wherein the $C_8$ aromatics stream (fresh feed) is additionally or alternatively introduced to the process directly to the isomerisation unit, directly to the molecular sieve membrane unit or both.

10. A process for recovering paraxylene from a $C_8$ aromatics stream containing paraxylene and at least one other isomer of xylene, ethylbenzene, or mixtures thereof which process comprises:

(a) recovering by means of a paraxylene separation process in a paraxylene recovery unit a portion of said paraxylene from at least a portion of said $C_8$ aromatics stream to produce a first stream having a reduced paraxylene content and containing a portion of said other isomers of xylene, said ethylbenzene, or mixtures thereof;

(b) passing at least a portion of said first stream directly or indirectly to a molecular sieve membrane unit comprising a molecular sieve membrane and optionally isomerisation catalyst under isomerization conditions, such that the permeate withdrawn through the molecular sieve membrane and from the molecular sieve membrane unit is enriched in ethylbenzene compared to the retentate;

(c) subjecting at least a portion of said permeate to an ethylbenzene isomerisation process in an ethylbenzene isomerisation unit to produce an isomerate having an enriched paraxylene content compared to that of the permeate;

(d) feeding the isomerate optionally combined with the retentate back to the paraxylene separation process.

11. A process as claimed in claim 10 wherein the isomerate from (c) optionally combined with the retentate is subjected to a further isomerisation process in a second isomerisation unit to produce a second isomerate having an enriched paraxylene content compared to the feed to the second isomerisation unit and feeding the second isomerate back to the paraxylene separation process.

12. A process as claimed in claim 10 which further comprises a zeolite membrane unit after (c) which produces a permeate enriched in paraxylene compared to the isomerate or second isomerate.

13. A process as claimed in claim 12 wherein the molecular sieve membrane unit introduced after (c) further comprises a xylenes isomerisation catalyst.

14. A process as claimed in claim 10 wherein there is present ethylbenzene isomerisation catalyst either as part of the molecular sieve membrane or downstream of the molecular sieve membrane but in close proximity to the membrane or both.

15. A process as claimed in claim 10 wherein the isomerisation catalyst in the molecular sieve membrane unit is located in close proximity to the membrane and on the permeate side of the membrane.

16. A process as claimed in claim 1 or 10 wherein the molecular sieve membrane unit comprises two or more alternating zones of catalyst and molecular sieve membrane.

17. A process as claimed in claim 1 or 10 wherein there are two or more molecular sieve membrane units with or without isomerisation catalyst arranged sequentially to each other.

18. A process as claimed in claim 1 which comprises a zeolite membrane which has been prepared by either the LAI-ISC, S-LAI-ISC or GEL-LAI-ISC processes.

19. A process for conversion of ethylbenzene to benzene and xylene isomers comprising:

a) passing at least a portion of a stream comprising ethylbenzene to a membrane unit comprising a molecular sieve membrane such that the permeate withdrawn through the molecular sieve membrane and from the molecular sieve membrane unit is enriched in ethylbenzene compared to the retentate; and b) passing at least a portion of said permeate to an ethylbenzene isomerization unit and converting at least a portion of said ethylbenzene to xylenes to produce an isomerate having an enriched paraxylene content compared to that of the permeate.

20. A process as claimed in claim 19 wherein the isomerate from (b) optionally combined with the retentate from (a) is subjected to a further isomerization process in a second isomerization unit to produce a second isomerate having an enriched paraxylene content compared to the feed to the second isomerization unit.

21. A process as claimed in claim 20 wherein said second isomerate is fed to a second molecular sieve membrane which produces a permeate enriched in paraxylene compared to said second isomerate.

* * * * *